(12) United States Patent
Hoernig

(10) Patent No.: US 11,399,789 B2
(45) Date of Patent: Aug. 2, 2022

(54) COMPRESSION UNIT FOR A COMBINED X-RAY AND ULTRASOUND EXAMINATION DEVICE, EXAMINATION DEVICE AND METHOD

(71) Applicant: SIEMENS HEALTHCARE GMBH, Erlangen (DE)

(72) Inventor: Mathias Hoernig, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 906 days.

(21) Appl. No.: 16/016,863

(22) Filed: Jun. 25, 2018

(65) Prior Publication Data

US 2018/0368796 A1 Dec. 27, 2018

(30) Foreign Application Priority Data

Jun. 23, 2017 (DE) .......................... 102017210604.2

(51) Int. Cl.
| *A61B 6/00* | (2006.01) |
| *A61B 8/08* | (2006.01) |
| *A61B 6/04* | (2006.01) |
| *A61B 8/00* | (2006.01) |
| *A61B 6/02* | (2006.01) |

(52) U.S. Cl.
CPC .............. *A61B 6/502* (2013.01); *A61B 6/025* (2013.01); *A61B 6/0414* (2013.01); *A61B 6/4417* (2013.01); *A61B 8/0825* (2013.01); *A61B 8/403* (2013.01); *A61B 8/4416* (2013.01); *A61B 8/4281* (2013.01)

(58) Field of Classification Search
CPC ................................. A61B 6/502; A61B 6/025
See application file for complete search history.

(56) References Cited

U.S. PATENT DOCUMENTS

| 6,102,866 A | 8/2000 | Nields et al. |
| 2015/0351706 A1* | 12/2015 | Nanke .................. A61B 6/0414 |
| | | 600/437 |
| 2017/0360389 A1 | 12/2017 | Ochiai et al. |

FOREIGN PATENT DOCUMENTS

| DE | 102014202955 A1 | 8/2015 |
| DE | 102015218607 A1 | 3/2017 |
| EP | 0936889 A2 | 8/1999 |
| WO | 9816149 A2 | 4/1998 |

* cited by examiner

*Primary Examiner* — Joseph M Santos Rodriguez
(74) *Attorney, Agent, or Firm* — Laurence A. Greenberg; Werner H. Stemer; Ralph E. Locher

(57) ABSTRACT

A compression unit for a combined x-ray and ultrasound examination device and an examination device. The handling of the combined x-ray and ultrasound examination device is simplified by providing a compression unit with a compression surface which is permeable to x-rays and ultrasound and which is, or can be, coupled to a support element of the examination device irrespective of the existence of a mechanical and/or electrical connection between the ultrasound unit and the examination device.

7 Claims, 2 Drawing Sheets

COMPRESSION UNIT FOR A COMBINED X-RAY AND ULTRASOUND EXAMINATION DEVICE, EXAMINATION DEVICE AND METHOD

CROSS-REFERENCE TO RELATED APPLICATION

This application claims the priority, under 35 U.S.C. § 119, of German patent application DE 10 2017 210 604.2, filed Jun. 23, 2017; the prior application is herewith incorporated by reference in its entirety.

BACKGROUND OF THE INVENTION

Field of the Invention

The invention relates to a compression unit for a combined x-ray/ultrasound examination device, to a combined x-ray/ultrasound examination device and to a method for replacing a compression unit combined x-ray/ultrasound examination device.

The prompt identification of breast cancer poses an enormous challenge for all currently existing medical imaging methods. There is a broad agreement in the overall medical field of research that a diagnosis can only be obtained with simultaneous sensitivity and specificity by the skillful combination of various imaging methods.

Both x-ray images and also ultrasound images are frequently used for a diagnosis using imaging methods.

An x-ray examination, e.g. a tomosynthesis, is generally carried out first. During the tomosynthesis, 2D x-ray images of a breast are recorded at various recording angles, for instance during a circular arc-shaped trajectory of the x-ray source about the object, and are calculated to form a 3D data record. On the basis of this 3D data record, slice recordings or x-ray images are then produced with any cutting approach by means of the 3D data record.

In order to be better able to assess a tissue change for a diagnosis, additional ultrasound images are then produced if necessary.

During an x-ray mammography examination the patient typically stands or sits directly in front of the x-ray examination device and the breast is compressed between two plates, whereas during an ultrasound examination (sonography) the patient lies on a patient couch and the breast is pushed against the ribcage by the ultrasound head. The patient must therefore be repositioned between the x-ray examination and the ultrasound examination. In addition, it is disadvantageous that during the x-ray examination and the ultrasound examination the breast is compressed to varying degrees and in different directions. It is a further disadvantage that the x-ray and the ultrasound images are recorded from different viewing directions and it is therefore difficult to overlay the images thus obtained as precisely as possible or connect them with one another.

Prototypes of combined x-ray/ultrasound examination devices are known. Examination devices are therefore known, for instance, in which a compression arrangement comprises a lower compression unit in the form of a bearing plate having the x-ray detector and an upper compression unit in the form of a compression plate, for instance a PMMA (e.g., Plexiglas®) plate. Devices of this type provide for an ultrasound examination of a breast, which is compressed between the upper compression plate and the lower bearing plate of the examination device. Here the ultrasound head required for the sonography is guided in a scanning movement along the tomosynthesis scanning direction across the topside of the compression plate. On account of the substantially unchanged compression of the breast during both imaging methods and on account of the defined viewing directions which can therefore be correlated with one another, the images obtained allow for an improved diagnosis.

Since the radiated ultrasound signals have to be coupled into the breast to be examined through the compression plate, it was proposed to use a compression recess with a flexible compression surface, instead of a rigid compression plate, wherein this flexible compression surface is formed with a fabric referred to as a gauze, for instance. During a compression the breast is shaped to be slightly convex by this embodiment of the compression recess. One advantage of this type of compression is a more homogenous distribution of the compression force onto the object to be examined and the possibility of an ultrasound examination immediately after an x-ray examination without the technical problems which would result from a coupling-in of the ultrasound through a compression plate.

With these examination devices it is essentially possible to use compression units of varying sizes. A first upper compression unit which interacts with the ultrasound head can be used with a small compression surface or alternatively a second upper compression unit with a large compression surface, for instance. It is disadvantageous, however, for the upper compression units each to comprise the entire mechanical and electrical activation of the ultrasound head, in other words in particular for the mechanism, the cabling and the motorized drive of the ultrasound head to be integrated into the compression units. This entails not only high installation costs of the individual compression units: A further problem involves the significant weight of the compression units during a replacement by operating personnel, and during handling, particularly when connecting the cable connections.

SUMMARY OF THE INVENTION

It is accordingly an object of the invention to provide a combined x-ray and ultrasound examination device and a compression unit for the device which overcome the above-mentioned and other disadvantages of the heretofore-known devices and methods of this general type and which simplify the handling of a combined x-ray/ultrasound examination device.

With the foregoing and other objects in view there is provided, in accordance with the invention, a compression unit for a combined x-ray and ultrasound examination device having an x-ray emitter, an x-ray detector, an ultrasound unit and a support element. The novel compression unit comprises:

a compression surface that is permeable to x-rays and ultrasound; and wherein the compression unit, irrespective of an existence of a mechanical and/or electrical connection between the ultrasound unit and the examination device, can be coupled to the support element of the examination device.

The advantages and embodiments explained below in connection with the compression unit apply analogously also to the inventive examination device and the inventive method and vice versa.

An inventive compression unit for a combined x-ray/ultrasound examination unit having an x-ray emitter, an x-ray detector and an ultrasound unit comprises a compression surface which is permeable to x-rays and ultrasound, and is wherein it can be coupled to a support element of the examination device irrespective of the existence of a mechanical and/or electrical connection between the ultrasound unit and the examination device.

With the above and other objects in view there is also provided, in accordance with the invention, a combined x-ray and ultrasound examination device, comprising:

an x-ray emitter, an x-ray detector and at least one support element;

an ultrasound unit connected or to be connected to said at least one support element or another unit of the examination device; and a compression unit having a compression surface that is permeable to x-rays and ultrasound;

wherein said at least one support element is configured such that said compression unit can be coupled to the support element irrespective of an existence of a mechanical and/or electrical connection between said ultrasound unit and the examination device.

In other words, the novel combined x-ray and ultrasound examination device comprises an x-ray emitter, an x-ray detector and at least one support element and an ultrasound unit which is or can be connected to the at least one support element or another unit of the examination device, and is wherein the at least one support element is embodied such that a compression unit can be coupled to the support element irrespective of the existence of a mechanical and/or electrical connection between the ultrasound unit and the examination device.

With the above and other objects in view there is also provided, in accordance with the invention, a novel method for changing a compression unit of a combined x-ray/ultrasound examination device having an x-ray emitter, an x-ray detector and an ultrasound unit. The compression unit coupled to a support element of the examination device is replaced irrespective of the existence of a mechanical and/or electrical connection between the ultrasound unit and the examination device.

A core concept of the invention is to release or separate from the compression unit the components of the compression unit which are required for the ultrasound examination, or in other words those components, the use of which is caused by the fact that the examination device is not a pure x-ray device but instead a combined x-ray/ultrasound examination device, in particular the heavy mechanical unit for moving the ultrasound unit and the ultrasound unit itself, and instead to provide these components permanently on a support element or another suitable unit of the examination device, wherein the support element is a stand (floor or ceiling stand) or a device column, a retaining arm or suchlike. The ultrasound unit with its mechanical and electrical activation, including the motorized drive, is therefore coupled separately from the compression unit to the support element of the examination device, while the compression unit is embodied separately and independently of the ultrasound unit. The ultrasound unit linked with the examination device together with its drive mechanism and electrics is therefore always kept unchanged, whereas the compression unit is designed to be replaceable. The compression unit therefore only comprises a few, generally comparatively light and cheap components, like a frame and a compression element held by the frame, which forms the compression surface.

The ultrasound unit is in particular an ultrasound transmitter, which interacts with a suitably positioned ultrasound receiver. However the ultrasound unit is preferably an ultrasound head (transducer), in other words an ultrasound probe, which sends and receives the ultrasound waves and converts these into electrical signals and forwards them for further processing. The term ultrasound head is used below as a preferred example of the ultrasound unit used.

Provision can be made in particular to configure the fabric held in the frame to be disposable. In this way, the fabric does not need to be laboriously cleaned of the contact gel after use. To this end the frame can be embodied such that the fabric is stretched therein, in particular have suitable stretching elements. The fabric can however also be glued to the frame or detachably fastened thereto in another way. Alternatively, the entire frame can also be embodied together with the fabric as a component which can be separated from the compression unit, and used only once.

The connection of the ultrasound head to the support element or another suitable unit of the examination device is carried out, similarly to the motorized propulsion of the ultrasound head, for the purpose of transferring the ultrasound head from an operating position into a replacement position and back and the corresponding activation of the drive, with the aid of suitable means, which are known to the person skilled in the art and therefore do not have to be explained further at this point.

With the present invention various compression units can be used with an examination device, which differ from one another in terms of size, shape, material and suchlike, without the afore-described problems known from the prior art occurring. In particular, it is now also possible with combined x-ray/ultrasound examination devices to use different compression units, in particular of a different size, selectively for individual patients and to replace them easily, in particular to individually take into account or support special clinical questions, an optimal breast positioning for specific cases and typical breast shapes. The inventive compression units described in more detail here can not only be connected to the examination device. Conventional compression units with flat, rigid compression surfaces, for instance made from Plexiglas, can also be used in specific cases, for instance if only an x-ray examination (mammography and/or tomosynthesis) of the breast, but not an ultrasound examination, is to take place.

Since the inventive compression units no longer have either the mechanical or the electrical activation of the ultrasound head, in particular no mechanism (such as e.g. guide rails, drive shafts or suchlike) for moving the ultrasound head along the compression surface during the scanning movement, no cabling for the ultrasound head and also no motorized drives, their manufacture is comparatively cheap. At the same time the handling of the examination device is also simplified, since a renewed connection of the cable connections of the ultrasound head is no longer necessary after replacing the compression unit. Furthermore, the weight of an inventive compression unit is significantly lower, as a result of which its handling by operating personnel is simplified during the replacement. In this way it is not only possible to replace the compression units more easily and quickly, but the clinical workflow is also simplified and improved.

The ultrasound head used can execute the desired ultrasound scan in conjunction with compression units which differ from one another in size and shape, and thus along scanning paths of varying lengths or within scanning regions of varying sizes, without a replacement of the drive unit of the ultrasound head or even only a brief electrical and/or mechanical decoupling (separation) of the drive unit being necessary.

It is also advantageous that by compressing the breast, such as takes place in order to carry out x-ray recordings (mammography and/or tomosynthesis), the breast is fixed at the same time. Since with the use of the inventive examination device neither the position nor the compression of the breast changes when the imaging modalities are replaced, both procedures can take place with the same positioning, as a result of which image contents can be correlated with one another comparatively simply.

In order to provide free access to the breast to be examined, compression units can be provided, which can be moved relative to the support element. In this connection, coupling facilities with a drive apparatus for the motorized propulsion of a coupled compression unit have proven to be of value.

It has proven particularly advantageous if the support element comprises an identification apparatus for automatically identifying various compression units. This feature can be used to automate the recording process.

Other features which are considered as characteristic for the invention are set forth in the appended claims.

Although the invention is illustrated and described herein as embodied in a compression unit for a combined x-ray/ultrasound examination device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

Figure 1:
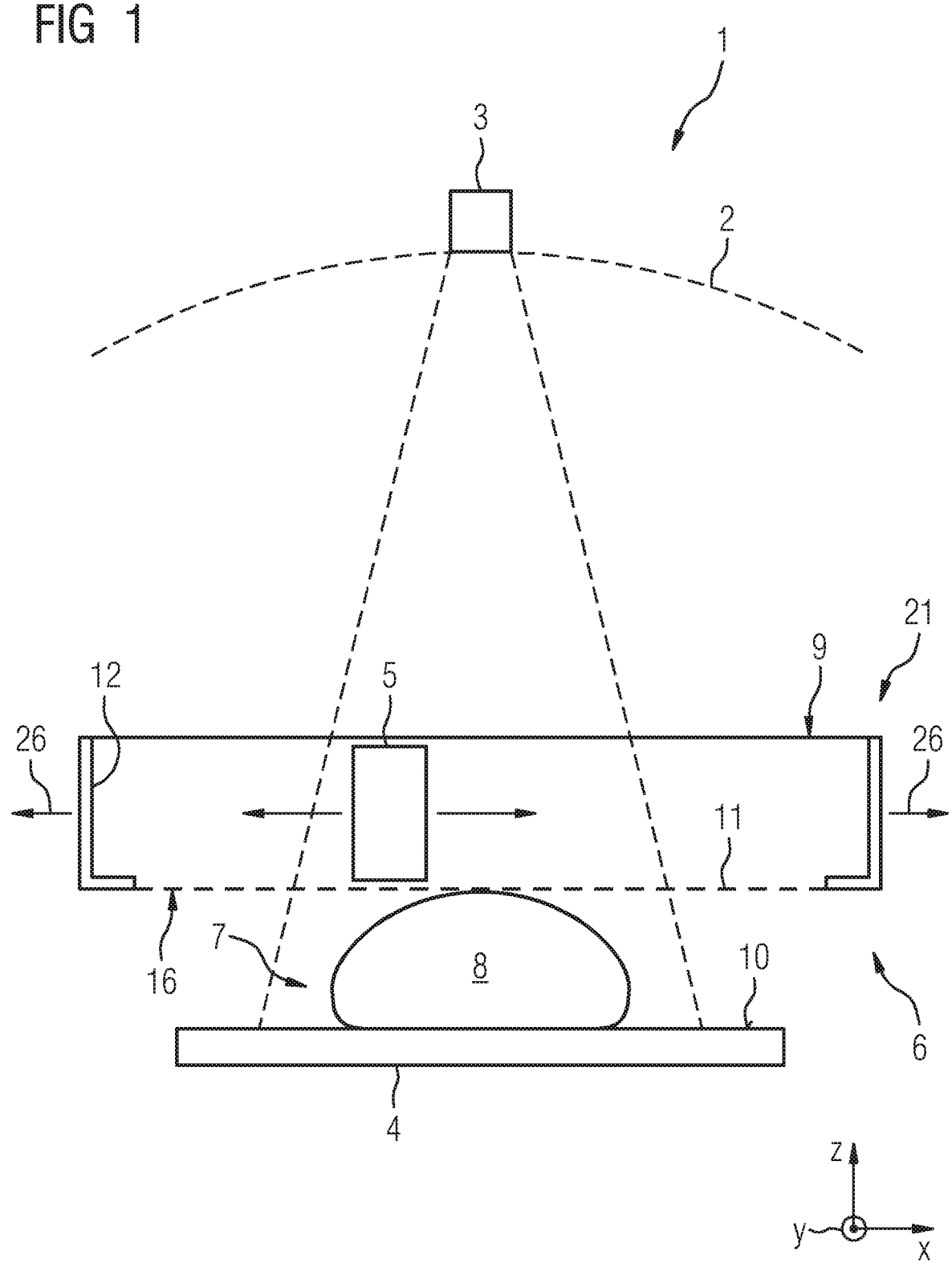
FIG. 1 shows a combined x-ray/ultrasound examination device from the front.

The figures illustrate the invention purely schematically and only with the primarily important components. The reference characters are used throughout to identify elements of identical or comparable function.

DETAILED DESCRIPTION OF THE INVENTION

Referring now to the figures of the drawing in detail and first, particularly, to FIG. 1 thereof, there is shown a schematic illustration of parts of a combined x-ray/ultrasound examination device 1, which is suited to carrying out mammography and tomosynthesis processes. This examination device 1 has an x-ray emitter 3 which can be moved along a trajectory 2, with an associated x-ray detector 4 and an ultrasound unit in the form of an ultrasound head 5.

The compression arrangement 6 comprises an upper compression unit and a lower compression unit. The compression units can be positioned on opposite sides of an examination region 7 disposed therebetween. The x-ray emitter 3 can be positioned such that its x-rays pass through the examination region 7 and then strike the detector 4. An x-ray beam which propagates in the direction of the detector 4 and emanates from the x-ray emitter 3 is shown in FIG. 1. During the x-ray recording the ultrasound head 5 is positioned outside of the x-ray beam.

In the present case, the detector 4, which can be embodied as a digital flat-panel detector, serves as a lower compression unit. The breast 8 of a patient is positioned directly on the detector 4 for a breast examination. With the upper compression unit—here in the form of a compression recess 9—the breast 8 to be examined is fixed and compressed between the compression recess 9 and the top side 10 of the detector 4. The compression recess 9 is embodied with a flexible compression element toward the detector 4 in the form of a fabric 11 (we use gauze in this context), which is stretched in a frame 12. This fabric 11 forms a compression surface 16 which is permeable to x-rays and ultrasound and is embodied to be applied to the breast 8. Here the fabric 11 is stretched substantially across the entire base region of the compression recess 9.

Figure 2:
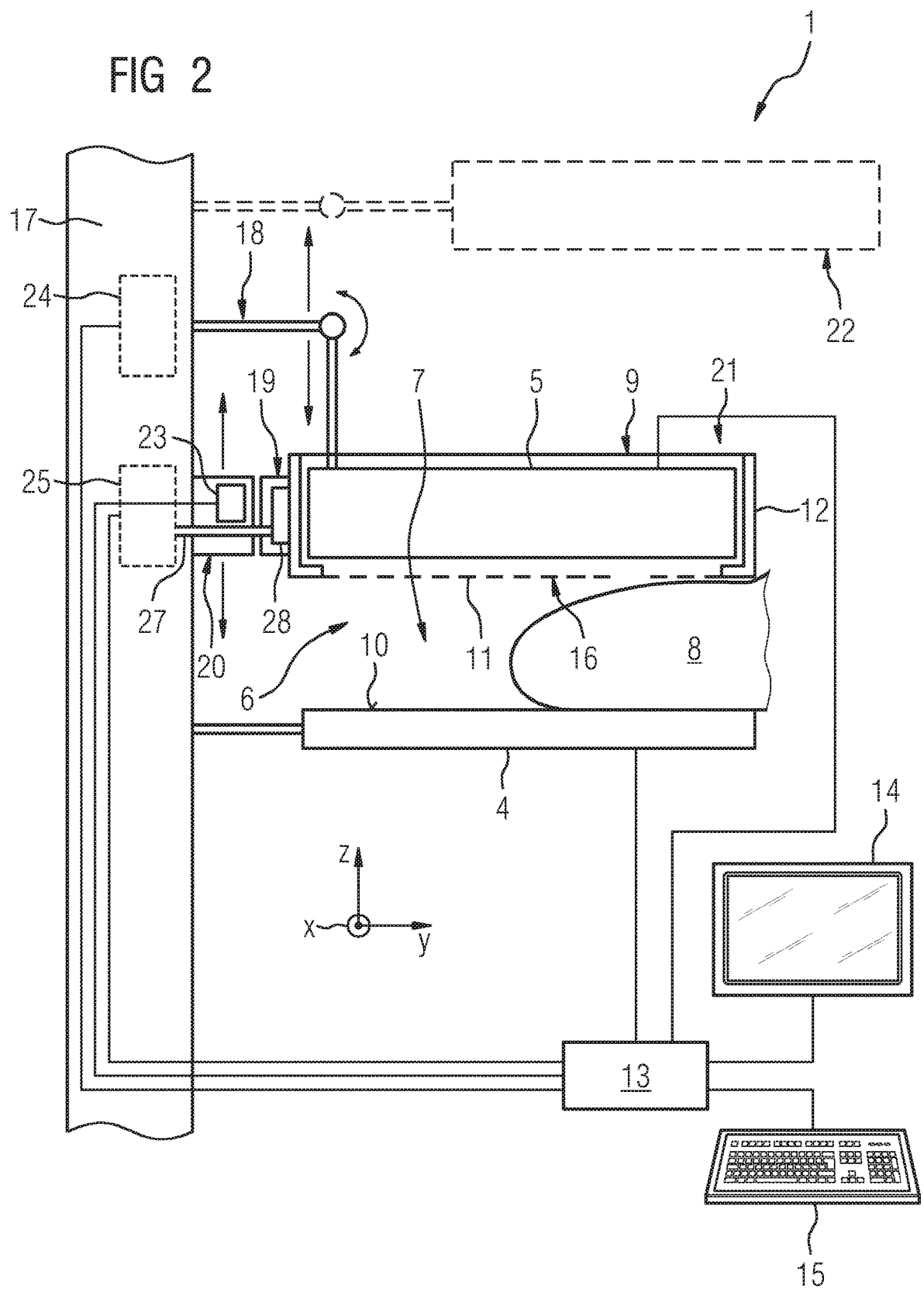
FIG. 2 shows a combined x-ray/ultrasound examination device from the side.

Referring now to FIG. 2, a control and computing unit 13 forms part of the examination device 1. The control and computing unit 13 has an associated monitor 14 and input unit 15. It serves to control the examination device 1, i.e. both to control the x-ray emitter 3 and the detector 4 and also to control the ultrasound head 5, and it is furthermore used for instance to execute image processing algorithms for 2D and/or 3D image generation.

Once the breast 8 has been compressed and fixed by the compression arrangement 6, first images of the breast 8 are recorded with the x-ray emitter 3 and the detector 4. While retaining the compression and fixing of the breast 8, second images can then be recorded with the aid of the ultrasound head 5. The compression of the breast 8 is retained during the image recordings and between the recording of the images, as are the position and the viewing angle of the respective recording.

The individual 2D x-ray images recorded with the detector 4 can be calculated in the control and computing unit 13 by means of a reconstruction method to form a 3D data record. X-ray images can be overlaid with ultrasound images. Suitable image processing serves to represent and overlay or fuse the various measurement results. It generates a visual presentation on the monitor 14 or another reproduction device. In this regard an x-ray image and an ultrasound image can be shown overlaid or synchronously, for instance. It is then particularly simple for a physician to analyze the examined breast tissue with unchanged locality on the basis of the x-ray and ultrasound images.

Various x-ray recordings (mammography, tomosynthesis) can be carried out alone or in combination with ultrasound recordings. An ultrasound recording can also take place independently of an x-ray recording.

FIG. 2 shows a schematic representation of a side view of an examination device 1. The detector 4 and the compression recess 9 are arranged on a vertical support element 17 of the examination device 1, here a stand. The x-ray emitter 3 can likewise be attached to the support element 17 or to a separate retaining arm (not shown) of the examination device 1. The compression units (detector 4 and compression recess 9) are mounted on the support element 17 such that the compression recess 9 can be lowered in order to compress a breast 9 located in the examination region 7. The detector 4 serves preferably as a static support, but can likewise be mounted in a height-adjustable manner.

The ultrasound head 5 which rests on the compression surface 16 and can be moved there horizontally and also vertically, i.e. guided across the fabric 11 lying on the breast 8, is positioned in the compression recess 9. This ultrasound head 5 is propelled and moved in a motorized manner, but completely independently of the compression recess 9. In other words, the ultrasound head 5 has its own guiding and movement unit 18 configured separately from the compression recess 9, attached at least partially in the support element 17, connected to the support element 17, with the aid of which the ultrasound head 5 is mechanically and electrically connected to the support element 17 and can be displaced horizontally in the plane, in the x- and/or y-direction, defined by the compression recess 9, and is removable from the compression recess 9.

The compression recess 9 has no mechanical and/or electrical components for driving the ultrasound head 5 at all. The compression recess can be coupled to the support element 17 of the examination device 1 with the aid of a correspondingly embodied coupling device 19 dedicated to the compression recess, irrespective of the existence, separation and/or creation of a mechanical and/or electrical connection between the ultrasound head 5 and the examination device 1, while retaining the mechanical and electrical connection between the ultrasound head 5 and the support element 17.

For this purpose, the support element 17 also has a corresponding coupling facility 20, which is embodied to couple the compression recess 9 to the support element 17, likewise irrespective of the existence, separation and/or creation of a mechanical and/or electrical connection between the ultrasound head 5 and the support element 17.

The ultrasound head 5 is therefore connected to the support element 17 independently of the compression recess 9, without using, i.e. separately from, the coupling facility 20 dedicated to the support element, for the compression recess 9.

As required, the ultrasound head 5 can be transferred, for instance pivoted, out of its operating position 21, shown in FIGS. 1 and 2, directly on or in the compression recess 9 into a replacement position 22 provided at a distance from the compression recess 9, in which replacement position 22 the compression recess 9 can be replaced. An ultrasound head 5, which is disposed in the replacement position 22, is shown with dashed lines in FIG. 2.

In order to replace the compression recess 9, the compression recess 9 is separated from the support element 17 of the examination device 1, for which purpose the existing mechanical connection is released between both units. Another compression recess 9 is then connected to the support element 17, for which purpose the mechanical connection is reestablished again between the other compression recess 9 and the support element 17. In order to form this mechanical connection, both the compression recesses 9 and also the support element 17 have suitable mechanical connection elements, embodied preferably to complement one another (e.g. for forming a rapidly releasable connection, in particular a latching, snap-fit and/or plug-in connection), which are not shown in detail in the figures. After such a replacement of the compression recess 9, the ultrasound head 5 is once again transferred out of its replacement position 22 into its operating position 21 in close proximity to the compression recess 9, in particular such that it is operationally ready, i.e. has assumed its start position, in which it rests directly on the compression surface 16 and establishes contact with the breast 8 via the fabric 11.

For improved coupling of the ultrasound waves to the breast 8, an ultrasound coupling gel (contact gel) can be applied to the respective compression element, here the fabric 11, by means of a dispensing unit (not shown).

The coupling facility 20 dedicated to the support element comprises sensors 23 for automatically identifying various compression recesses 9. The identification mechanism used can comprise, for instance, an optical identifier (e.g. a barcode) and/or an electrical or electronic identifier (e.g. by means of RFID technology). In this regard, data of the coupled compression recess 9 which is automatically read out or identified is transferred to the examination device 1, more precisely the control and computing unit 13, preferably during the coupling of the compression recess 9, in other words when the mechanical connection is established between the compression recess 9 and the support element 17, in particular by means of the coupling facility 20 dedicated to the support element, which for this purpose has suitable sensors 23 or suchlike. This data involves in particular details relating to the shape and/or size of the compression recess 9, such as, for instance, the available scanning region (scanning length and width) and the start and stop position of the ultrasound head 5 for this special compression recess 9. This data is then used by the control and computing unit 13 to activate the ultrasound head 5, in particular to transfer the ultrasound head 5 into the precise start position of a newly coupled compression recess 9, to control the subsequent scanning movement of the ultrasound head 5 along the fabric 11 and to terminate the scan and hold the ultrasound head 5 in the stop position.

The motorized drives 24, 25 provided to move the ultrasound head 5 and the compression recess 9 are only indicated in FIG. 2.

The two coupling facilities 19, 20 of the compression recess 9 and the support element 17 are preferably arranged such that the compression recess 9 coupled to the support element 17 is disposed exactly symmetrically with respect to the x-ray emitter 3 and the detector 4. However compression recesses 9 are also possible which have deviating coupling facilities (not shown) such that a compression recess 9 coupled to the support element 17 is disposed eccentrically with respect to the x-ray emitter 3 and the detector 4. This is useful in particular if better one-sided access to the breast 8 to be examined is to be provided for reasons of the medical workflow. A compression recess 9 can have normal (for instance centrally arranged), but simultaneously also deviating (for instance eccentrically arranged) coupling facilities 19, so that, assuming a corresponding embodiment of the coupling facility 20 of the support element 17, it can be used when positioned both symmetrically and also non-symmetrically.

In particular, with compression recesses 9 with coupling facilities 19 for non-symmetrical positioning, but also with other compression recesses 9, it is advantageous if the compression recess 9 can be moved manually or using a motor laterally, i.e. in the plane of the contact surface, relative to the detector 4, as indicated in FIG. 1 by the arrow 26. In the event that a motorized displacement of the compression recess 9 is intended, the coupling facilities 19, 20 preferably comprise suitable drive facilities for transmitting a motorized propulsion force from a motorized drive 25 provided in the support element 18 to the coupled compression recess 9. Here the drive facilities comprise for instance a (flexible) shaft 27 which can be propelled by a drive 25 accommodated in the support element 17, and which drives the compression recess 9 to move laterally by way of coupling facilities 20, 19 between the support element 17 and compression recess 9 which are connected to one another, possibly with the involvement of a drive mechanism contained in the compression recess 9, for instance a guiding and/or transmission element 28. When the compression recess 9 has reached the desired lateral movement position asymmetrically to the detector 4, it remains there while the images are being recorded.

Although the invention has been illustrated and described in detail using the preferred exemplary embodiment, the invention is not limited to the disclosed examples and other variations can be derived therefrom by the person skilled in the art without departing from the scope of protection of the invention. In particular, the details provided in connection with the use of compression recesses also apply at all times to other types of compression units.

The following is a summary list of reference numerals and the corresponding structure used in the above description of the invention:

1 examination device
2 trajectory
3 x-ray emitter
4 x-ray detector, detector
5 ultrasound unit, ultrasound head
6 compression arrangement
7 examination region
8 object, breast
9 compression unit, compression recess
10 detector top side
11 compression element, fabric
12 frame
13 control and computing unit
14 monitor
15 input unit
16 compression surface
17 support element, stand
18 guiding and moving unit
19 coupling facility of the compression recess
20 coupling facility of the support element
21 operating position
22 replacement position
23 sensor
24 motorized drive of the ultrasound head
25 motorized drive of the compression recess
26 lateral displacement movement of the compression recess
27 drive shaft
28 guiding and/or transmission element

The invention claimed is:

1. A compression unit for a combined x-ray and ultrasound examination device having an x-ray emitter, an x-ray detector, an ultrasound unit and a support element, the compression unit comprising:
   a compression surface that is permeable to x-rays and ultrasound, said compression surface formed from a fabric, said fabric arranged so that, in use an ultrasound operation is performed over the fabric;
   the compression unit having no mechanical and/or electrical components for driving the ultrasound unit, the compression unit including a dedicated coupling device for coupling the compression unit to the support element irrespective of an existence of a mechanical and/or electrical connection between the ultrasound unit and the examination device; and
   the compression unit including an identifier readable by a sensor of the support element for automatically identifying the compression unit when coupled with the support element.

2. The compression unit according to claim 1, comprising a coupling facility configured to couple the compression unit to the support element of the examination device irrespective of the existence of a mechanical and/or electrical connection between the ultrasound unit and the examination device.

3. The compression unit according to claim 1, configured with parts embodied for single use.

4. A combined x-ray and ultrasound examination device, comprising:
   an x-ray emitter, an x-ray detector and at least one support element;
   an ultrasound unit connected or to be connected to said at least one support element or another unit of the examination device; and
   a compression unit having a compression surface that is permeable to x-rays and ultrasound, said compression surface formed from a fabric, said fabric arranged so that, in use an ultrasound operation is performed over the fabric, said compression unit having no mechanical and/or electrical components for driving the ultrasound unit;
   said compression unit including a coupling device dedicated to said compression unit and configured to couple said compression unit to the support element irrespective of an existence of a mechanical and/or electrical connection between said ultrasound unit and the examination device; and
   a coupling facility dedicated to the support element, said coupling facility including at least one sensor configured to identify said compression unit and/or read out data of said compression unit and to transfer the identity and/or data to the examination device.

5. The combined x-ray and ultrasound examination device according to claim 4, wherein said coupling facility is also configured to couple said compression unit to said support element irrespective of the existence of a mechanical and/or electrical connection between said ultrasound unit and the examination device.

6. The combined x-ray and ultrasound examination device according to claim 5, wherein said coupling facility comprises a drive facility for a motorized propulsion of said compression unit when said compression unit is coupled to said support element.

7. A method for replacing a compression unit of a combined x-ray and ultrasound examination device, the examination device having an x-ray emitter, an x-ray detector, an ultrasound unit and a compression unit, the method comprising:
   replacing a compression unit that is coupled to a support element of the examination device irrespective of an existence of a mechanical and/or electrical connection between the ultrasound unit and the examination device, the compression unit including a compression surface formed from a fabric, the fabric arranged so that, in use an ultrasound operation is performed over the fabric, the compression unit having no mechanical and/or electrical components for driving the ultrasound unit;
   identifying the replaced compression unit and/or reading out data of the replaced compression unit with a sensor of a coupling facility dedicated to the support element; and
   transferring the identity and/or data to the examination device.

* * * * *